United States Patent
Eberhardt et al.

(10) Patent No.: US 7,141,687 B2
(45) Date of Patent: Nov. 28, 2006

(54) N'-SUBSTITUTED N-ACYLAMIDINE METAL TRANSITION COMPLEXES AND THEIR USE AS CATALYSTS

(75) Inventors: Jan Kurt Eberhardt, Oldenburg (DE); Ernst-Ulrich Würthwein, Münster (DE)

(73) Assignee: BASF Aktiengesellschaft (DE)

(*) Notice: Subject to any disclaimer, the term of this patent is extended or adjusted under 35 U.S.C. 154(b) by 0 days.

(21) Appl. No.: 10/537,569

(22) PCT Filed: Nov. 28, 2003

(86) PCT No.: PCT/EP03/13467

§ 371 (c)(1),
(2), (4) Date: Jun. 3, 2005

(87) PCT Pub. No.: WO2004/050670

PCT Pub. Date: Jun. 17, 2004

(65) Prior Publication Data

US 2006/0069275 A1    Mar. 30, 2006

(30) Foreign Application Priority Data

Dec. 4, 2002 (DE) ................ 102 56 854

(51) Int. Cl.
C07F 15/00 (2006.01)
C07F 1/08 (2006.01)
B01J 31/00 (2006.01)
C07C 2/00 (2006.01)

(52) U.S. Cl. ............. 556/32; 556/33; 585/422; 585/425; 585/457; 502/165; 502/166; 502/167

(58) Field of Classification Search ............... 556/32, 556/33; 502/165, 166, 167; 585/422, 425, 585/457

See application file for complete search history.

(56) References Cited

U.S. PATENT DOCUMENTS 2,196,447 A * 4/1940 Van Peski .................... 556/33
5,703,269 A  12/1997 Herrmann et al.

FOREIGN PATENT DOCUMENTS

EP        0 719 758        7/1996

OTHER PUBLICATIONS

Hiraki, K. et al., "Formation of N-imidoylimidatoruthenium(II) complexes via Ruthenium-Promoted Hydration of Nitriles", J. Chem. Soc., Dalton Trans. (1996), pp. 291-298.

Hillier, A. C. et al., "Mini Review: Catalytic Cross-Coupling Reactions Mediated By Palladium/Nucleophilic Carbene Systems", Journal of Organometallic Chemistry 653 (2002), pp. 69-82.
Buchmeiser, M. R. et al., "Bis(pyrimidine)-Based Palladium Catalysts: Synthesis, X-ray Structure and Applications in Heck-, Suzuki-, Sonogashira-Hagihara Couplings and Amination Reactions", Journal of Organometallic chemistry 634 (2001), pp. 39-46.
Eberhardt, J. K. et al., "Unsaturated Hetero Chains, IX 1:1- and 2:1-Copper(II) Complexes From Primary N-Acylamidines", Eur. J. Inorg. Chem (2000), pp. 1739-1743.
Bart, J.C.J. et al., "Preparation and Crystal Structure of Bis-(benzoylbenzamidine)nickel(II)", Inorganica Chimica Acta, 28 (1978), pp. 201-210.
Konakahara, T. et al., "Stereoselective Synthesis of trans-2-Aryl-3-(2-pyridyl)aziridines From An α-Silyl Carbanion", J. Chem. Soc., Perkins Trans. (1987), pp. 1489-1493.
Fu and Littke, "Palladiumkatalysierte Kupplungen von Arylchloriden", Angew. Chem. (2002) vol. 114, pp. 4350-4386.
Herrmann, "N-Heterocyclische Carbene: ein neues Konzepl in der metallorganischen Katalyse", Angew. Chem. (2002) vol. 114, pp. 1342-1363.

* cited by examiner

Primary Examiner—Porfirio Nazario-Gonzalez
(74) Attorney, Agent, or Firm—Connolly Bove Lodge & Hutz

(57) ABSTRACT

The invention relates to N'-substituted N-acylamidine transition metal complexes of the general formula (I), wherein M represents a transition metal, selected from the group of metals including Ni, Cu, Ru, Rh, Pd, Os, Ir and Pt, X represents Cl, Br, triflate, methane sulfonate or p-toluol sulfonate, m is 0, 1 or 2, n is 1, 2 or 3 and the radicals have the following meanings: $R^1$, $R^2$ is a straight-chain or branched, cyclic hydrocarbon group with 1 to 20 carbon atoms which can be mono or poly-unsaturated, an aromatic group with 3 to 6 chain members, which is linked directly or via a $C_1$ to $C_6$ alkyl or $C_2$ to $C_6$ alkylene group, whereby the mentioned groups can carry one or more substituents. Ar represents $C_6$ to $C_{10}$ aryl or hetaryl with 5 to 10 ring members, whereby the mentioned groups can be substituted by $C_1$ to $C_6$ alkyl, $C_1$ to $C_4$ halogenalkyl, $NR^{10}R^{11}$, $COOR^6$, $Si(R^7)_3Si(R^7)_2R^8$, $OR^3$ and/or halogen. The invention also relates to a method for producing this new class of metal transition complexes and their use as catalysts (I)

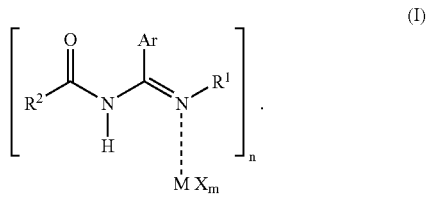

17 Claims, No Drawings

N'-SUBSTITUTED N-ACYLAMIDINE METAL TRANSITION COMPLEXES AND THEIR USE AS CATALYSTS

RELATED APPLICATIONS

This application is a national stage application (under 35 U.S.C. 371) of PCT/EP2003/013467 filed Nov. 28, 2003 which claims benefit to German application 102 56 854.5 filed Dec. 4, 2002.

The present invention relates to N'-substituted N-acylamidine-transition metal complexes of the general formula I

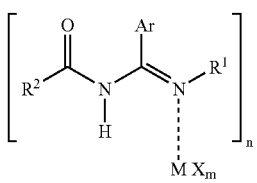

where
M is a transition metal selected from the group of the metals Ni, Cu, Ru, Rh, Pd, Os, Ir and Pt
X is Cl, Br, triflate, methanesulfonate or p-toluenesulfonate
m is 0, 1 or 2,
n is 1, 2 or 3
and the radicals are defined as follows:
$R^1$, $R^2$ are each a straight-chain, branched or cyclic hydrocarbon radical having from 1 to 20 carbon atoms which may be mono- or polyunsaturated, an aromatic radical having from 3 to 6 ring members which may be bonded directly or via a $C_1$- to $C_6$-alkyl or $C_2$- to $C_6$-alkylene group, and the radicals mentioned may bear one or more substituents selected from the group of $C_1$- to $C_6$-alkyl, $C_1$- to $C_4$-haloalkyl, $OR^3$, $NR^4R^5$, $COOR^6$, $Si(R^7)_3$, $Si(R^7)_2R^8$, halogen, aryl, $C_3$-$C_8$-cycloalkyl,
$R^3$, $R^6$, $R^8$ are each independently $C_1$- to $C_{12}$-alkyl, $C_7$- to $C_{12}$-aralkyl, $C_6$- to $C_{10}$-aryl, $C_3$- to $C_8$-cycloalkyl, $C_3$- to $C_8$-cycloalkyl in which one $CH_2$ group has been replaced by O, NH or $NR^9$, and $R^4$ and $R^5$ may together also be —$(CH_2)_y$—, where y is an integer from 4 to 7, hetaryl or hetaralkyl having from 5 to 6 ring members in the heteroaromatic,
$R^4$, $R^5$ and $R^{10}$, $R^{11}$ are each independently hydrogen, straight-chain or branched $C_1$- to $C_{12}$-alkyl, $C_7$- to $C_{12}$-aralkyl, $C_6$- to $C_{10}$-aryl, $C_3$- to $C_8$-cycloalkyl or $C_3$- to $C_8$-cycloalkyl in which one $CH_2$ group has been replaced by O, NH or $NR^9$, and $R^4$ and $R^5$ and/or $R^{10}$ and $R^{11}$ may each together be —$(CH_2)_y$—, where y is an integer from 4 to 7;
$R^7$, $R^9$ are each independently straight-chain or branched $C_1$- to $C_{12}$-alkyl or $C_7$- to $C_{12}$-aralkyl,
Ar is $C_6$-$C_{10}$-aryl or hetaryl having from 5 to 10 ring members, and the radicals mentioned may be substituted by $C_1$- to $C_6$-alkyl, $C_1$- to $C_4$-haloalkyl, $NR^{10}R^{11}$, $COOR^6$, $Si(R^7)_3$, $Si(R^7)_2R^8$, $OR^3$ and/or halogen.

The invention further relates to a process for preparing this novel class of transition metal complexes and to their use as catalysts for organic reactions, in particular for coupling reactions, in which new bonds are formed between carbon atoms or between carbon atoms and heteroatoms.

Organic and inorganic transition metal compounds have become indispensable as reagents or catalysts in modern organic synthetic chemistry. A significant portion of the reactions available today as tools in the synthesis of complex organic structures is based on the diverse reactivity patterns of transition metal-organic compounds. Particular importance has been gained by synthetic methods and catalyst systems which help to form new bonds between carbon atoms. These transition metal-catalyzed coupling reactions have in the meantime also gained considerable economic importance and are therefore still the subject-matter of intensive research efforts.

The current state of the art on transition metal-catalyzed coupling reactions is summarized in numerous publications. Examples cited here include F. Diederich et al., Metal-catalyzed Cross-coupling Reactions, Wiley-VCH, Weinheim, 1998 and L. Brandsma et al., Application of Transition Metal Catalysts in Organic Synthesis, Springer, New York, 1998. A current review is also given by G. C. Fu et al. in Angew. Chem. 2002, 114, 4350–4386.

In most of the homogeneous transition metal catalyst systems described hitherto, the catalytically active transition metal central atom is stabilized by ligands having weak donor properties. Predominant among these are phosphine ligands, in particular tertiary phosphines. An alternative to the oxidation- and temperature-sensitive phosphine ligands developed only recently is constituted by ligand systems whose donor properties can be attributed directly or indirectly to nitrogen atoms.

For instance, W. A. Herrmann et al., Angew. Chem. 2002, 114, 1342–1363, describe N-heterocyclic palladium-dicarbene compounds and their use as catalysts in the coupling of donor-substituted bromoarenes with styrene.

EP-A-0 719 758 describes the preparation of aromatic olefins from haloaromatics and olefins by Heck reaction in the presence of palladium complexes which contain heterocyclic carbene ligands as catalysts.

A. C. Hillier et al. in J. Organomet. Chem. 2002, 653, 69–82 describe palladium compexes with monomeric imidazol-1-ylidene ligands, which can be used to couple bromoaromatics with butyl acrylate.

A bidentate bipyrimidyl ligand for stabilizing a palladium catalyst is described by M. R. Buchmeister et al. in J. Organomet. Chem. 2001, 634, 39–46. This allows catalysis of coupling reactions of styrene or ethyl acrylate with differently substituted bromoarenes.

N-Acyl-N'-alkyl-transition metal complexes have not yet been described. In contrast, N-acylamidines are known. For instance, E.-U. Würthwein et al. in Eur. J. Inorg. Chem. 2000, 1739–1743 describe four N-acylamidine-copper(II) complexes in which the copper atom is bonded via the acyl oxygen and the nonalkylated amidine nitrogen.

A nickel(II) complex described by J. C. J. Bart et al., Inorganica Chimica Acta, 28 (1978), 201–210 has the same coordination. In this case, the central atom is complexed by two anionic N-acylamidine ligands.

Owing to the outstanding economic importance which transition metal-catalyzed C—C bond-forming coupling reactions have gained, there is still a need for improved catalyst systems. The main interest attaches firstly to the development of catalysts having relatively high catalytic activity which is manifested on the industrial scale in high turnover numbers and thus an improved space-time yield. Secondly, there is still a desire for catalysts having low substrate specificity, i.e. catalysts which are suitable for converting a very broad spectrum of substrates. These catalysts should additionally be obtainable readily, inexpensively and on the industrial scale.

A novel class of transition metal complexes of the general formula I as defined at the outset has now been found.

The $R^1$ and $R^2$ radicals may each independently be a straight-chain, branched or cyclic hydrocarbon radical having from 1 to 20 carbon atoms which may be mono- or polyunsaturated, an aromatic radical having from 6 to 14 ring members which may be bonded directly or via a $C_1$- to $C_6$-alkyl or $C_2$- to $C_6$-alkylene group. For example, $R^1$ and $R^2$ may be defined as follows:

$C_1$- to $C_6$-alkyl: methyl, ethyl, n-propyl, 1-methylethyl, n-butyl, 1-methylpropyl, 2-methylpropyl and 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-methylbutyl, 3,3-dimethylbutyl, 1-ethylbutyl, 2-ethylbutyl, 1,1,2-trimethylpropyl, 1-ethyl-1-methylpropyl and 1-ethyl-3-methylpropyl;

$C_1$- to $C_{12}$-alkyl such as $C_1$- to $C_6$-alkyl (as specified above) or unbranched or branched heptyl, octyl, nonyl, decyl, undecyl or dodecyl, $C_2$- to $C_6$-alkenyl: for example, ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl -3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl -2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

$C_3$- to $C_8$-cycloalkyl: for example, cyclopropyl, cyclobutyl, cyclopentyl, cyclohexyl, cycloheptyl and cyclooctyl;

aryl: mono- to tricyclic aromatic carbocycle having from 6 to 14 ring members, for example phenyl, naphthyl and anthracenyl;

$C_7$- to $C_{12}$-aralkyl, for example phenylmethyl, 1-phenylethyl, 2-phenylethyl, 1-phenylpropyl, 2-phenylpropyl or 3-phenylpropyl.

These $R^1$ and $R^2$ radicals may optionally be substituted, and the substituents may be varied within a wide range. Possible substituents are in particular:

$C_1$- to $C_6$-alkyl (as specified above) and additionally $C_1$- to $C_4$-haloalkyl: a $C_1$- to $C_4$-alkyl radical which is partly or fully substituted by fluorine, chlorine, bromine and/or iodine, i.e., for example, chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl and nonafluorobutyl.

The $R^1$ and $R^2$ radicals may also bear substituents such as alkoxy, alkoxycarbonyl and/or amino substituents, for example $C_1$- to $C_4$-alkoxy such as methoxy or ethoxy, $C_2$- to $C_6$-alkoxycarbonyl such as methoxycarbonyl or ethoxycarbonyl, or $NH_2$, di-$C_1$- to $C_4$-alkylamino such as dimethylamino or diethylamino, or $C_1$- to $C_4$-alkylamino such as methylamino or ethylamino. The $R^3$ to $R^6$, $R^8$, $R^{10}$ and $R^{11}$ radicals follow the above-cited definitions and can additionally be defined as follows:

$C_6$- to $C_{10}$-aryl: phenyl and naphthyl and also 3- to 6-membered heterocyclyl, for example 2-oxiranyl, 2-oxetanyl, 3-oxetanyl, 2-tetrahydrofuranyl, 3-tetrahydrofuranyl, 2-tetrahydropyranyl, 3-tetrahydropyranyl and 4-tetrahydropyranyl, 2-azirinyl, 2-, 3-tetrahydropyranyl, 3-tetrahydropyranyl and 4-tetrahydropyranyl.

The $R^7$ and $R^9$ radicals are each independently straight-chain or branched $C_1$- to $C_{12}$-alkyl or $C_7$- to $C_{12}$-aralkyl as defined above.

$R^1$ and $R^2$ are preferably branched or unbranched $C_1$- to $C_{12}$-alkyl, $C_7$- to $C_{12}$-aralkyl, $C_6$- to $C_{10}$-aryl, and the radicals may each be substituted by up to three halogen atoms and/or one or two $C_1$-$C_6$-alkyl, trifluoromethyl and/or $C_1$-$C_6$-alkoxy substituents.

Very particularly preferred $R^1$ radicals are branched or unbranched $C_1$- to $C_{12}$-alkyl, in particular $C_1$- to $C_6$-alkyl, and $C_7$- to $C_{12}$-aralkyl, for example benzyl or phenylethyl.

$R^2$ is more preferably branched or unbranched $C_1$- to $C_{12}$-alkyl, in particular $C_1$- to $C_6$-alkyl, $C_7$- to $C_{12}$-aralkyl or $C_6$- to $C_{10}$-aryl, and the aromatic radicals as specified above may be substituted by from one to three halogen atoms and/or one or two $C_1$- to $C_6$-alkyl, $C_1$- to $C_4$-haloalkyl such as trifluoromethyl, or $C_1$- to $C_6$-alkoxy substituents.

The aromatic radical of the amidine hydrocarbon Ar may be varied widely and is a 5- to 14-membered aromatic or heteroaromatic radical having from 2 to 14 carbon atoms which may optionally be substituted by one or more $C_1$- to $C_6$-alkyl, $C_1$- to $C_6$-alkoxycarbonyl, $C_1$- to $C_6$-alkoxy, trialkylsilyl, diarylalkylsilyl and/or trifluoromethyl substituents, and/or halogen such as fluorine, chlorine or bromine. Ar is preferably a 5- to 10-membered aromatic or heteroaromatic radical having from 2 to 10 carbon atoms. Possible examples thereof are: 2-furyl, 3-furyl, 3-thienyl, 2-pyrrolyl, 3-pyrrolyl, 3-isoxazolyl, 4-isoxazolyl, 5-isoxazolyl, 4-isothiazolyl, 3-pyrazolyl, 4-pyrazolyl, 5-pyrazolyl, 2-oxazolyl, 4-oxazolyl, 5-oxazolyl, 2-imidazolyl, 4-imidazolyl, 1,2,4-oxadiazol-3-yl, 1,2,4-oxadiazol-5-yl, 1,2,4-triazol-3-yl, 1,3,4-oxadiazol-2-yl, 1,3,4-triazol -2-yl; 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl; 2-furyl, 3-furyl, 2-pyrrolyl, 3-pyrrolyl, 3-isoxazolyl, 4-isoxazolyl, 5-isoxazolyl, 4-isothiazolyl, 5–3-pyrazolyl, 4-pyrazolyl, 5-pyrazolyl, 2-oxazolyl, 4-oxazolyl, 5-oxazolyl, 2-imidazolyl, 4-imidazolyl, 1,2,4-oxadiazol-3-yl, 1,2,4-oxadiazol-5-yl, 1,2,4-triazol-3-yl, 1,3,4-oxadiazol-2-yl, and 1,3,4-triazol-2-yl; 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl, each of which may optionally be substituted by one or more $C_1$- to $C_6$-alkyl, $C_1$- to $C_6$-alkoxycarbonyl, $C_1$- to $C_6$-alkoxy, trialkylsilyl, diarylalkylsilyl and/or $C_1$- to $C_4$-haloalkyl substituents and/or halogen. Very particular preference is given to Ar being a 5- or 6-membered heteroaromatic radical having from 2 to 6 carbon atoms and oxygen and/or nitrogen as heteroatoms, said radical optionally being substituted by one or more $C_1$- to $C_6$-alkyl, $C_1$- to $C_6$-alkoxy, trialkylsilyl such as trimethylsilyl and/or $C_1$-$C_4$-haloalkyl such as trifluoromethyl substituents and/or halogen.

In this context, halogen refers to the elements fluorine, chlorine, bromine and/or iodine, in particular fluorine or chlorine.

M is preferably a transition metal selected from the group of the metals Ru, Rh, Pd, Os, Ir and Pt, most preferably Pd or Pt.

The number of ligands X present in the transition metal compounds according to the invention is determined by the valency of the central atom selected and the number of amidine ligands present. In the general formula I, m preferably takes the value 1 or 2.

The number of amidine ligands of the general formula III

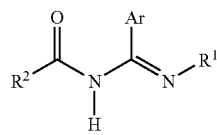

present in the transition metal compounds according to the invention is determined in a similar manner the valency of the central atom selected and the number and also the charge of the ligands X present. In the general formula I, n is preferably 1 or 2, more preferably 2.

Very particular preference is given to compounds of the general formula I in which M is Pd, X is Cl, n is 2 and m is 2. Among this group of compounds, preference is given in particular to those in which $R^1$ is straight-chain or branched $C_1$- to $C_{12}$-alkyl which may optionally be substituted by from one to three halogen atoms and/or one or two methyl, trifluoromethyl and/or $C_1$- to $C_6$-alkoxy substituents, and $R^2$ is straight-chain or branched $C_1$- to $C_{12}$-alkyl which may optionally be substituted by from one to three halogen atoms and/or one or two methyl, trifluoromethyl and/or $C_1$- to $C_6$-alkoxy substituents, or is a $C_7$ to $C_{12}$-aralkyl or $C_6$— to $C_{10}$-aryl, and the aromatic radicals may be substituted by from one to three halogen atoms and/or one or two $C_1$- to $C_6$-alkyl, trifluoromethyl and/or $C_1$- to $C_6$-gen atoms and/or one or two $C_1$- to $C_8$-alkyl, trifluoromethyl and/or $C_1$- to $C_6$-alkoxy substituents.

The invention further relates to a process for preparing N'-substituted N-acylamidine-transition metal complexes of the general formula I by reacting N'-substituted N-acylamidines with suitable compounds, which are typically soluble in organic solvents, of the particular transition metals.

The N-substituted amidines of the general formula II

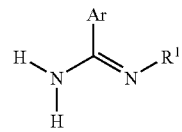

required for the synthesis of the transition metal complexes according to the invention can be prepared according to T. Konakahara et al. (J. Chem. Soc. Perkin Trans. 1, 1987, 1489–1494) and also according to J. K. Eberhardt, Diploma dissertation, University of Münster, 1999, by reacting primary amines with aromatic nitriles. To this end, a solution of the primary amine in an ethereal solvent such as ether or tetrahydrofuran is initially charged and an approximately equimolar amount based on the amine used of a base sufficiently strong to deprotonate the amine is added with cooling. Typically, the concentration of the solution of the amine is between about 0.5 and about 5 mol/l. Suitable bases are, for example, alkyllithium compounds or hydrides, each as such or in the form of solutions or suspensions, preferably n-butyllithium in dissolved form. The base is advantageously added with cooling, typically to temperatures below about −30° C., preferably at temperatures below about −70° C.

Subsequently, a likewise approximately equimolar amount based on the amine used of a nitrile is likewise added dropwise with cooling. The reaction is at temperatures below −50° C., preferably below −70° C., and is typically complete after from 1 to 2 h. After heating to room temperature, the reaction mixture is hydrolyzed by adding water or a suitable protic solvent such as methanol or ethanol or aqueous mixtures thereof.

Alternatively, according to P. Luhhardt, Thesis, University of Münster, 1989, N-substituted amidines of the general formula II can be prepared by adding a primary amine with ice cooling to a mixture of anhydrous aluminum trichloride ($AlCl_3$) and an approximately equimolar amount of a nitrile, in an approximately equimolar amount based on the other two reactants. The reaction mixture is subsequently heated to temperatures above 100° C., preferably above 150° C. The reaction is completed typically after from about 0.5 to 3 h.

The reaction mixture is advantageously worked up by pouring the melt onto a precooted dilute mineral acid solution, admixing with activated carbon and stirring. After filtration and extractive workup, the N-substituted amidines prepared in this way are purified by fractional distillation.

Amidines of the general formula II can, for example, be acylated to N'-substituted N-acylamidines of the general formula III

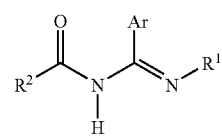

by dissolving the particular N-substituted amidine in 2 M sodium hydroxide solution and, at a temperature below 10° C. and based on the amount of the amidine used, adding from about 0.8 to about 1 equivalent of a suitable acylating agent as such or in dissolved form, preferably dissolved in acetone. The reaction is advantageously carried out at temperatures of up to 10° C. and is complete typically after from 0.5 to 4 h. Depending on their properties, the N'-substituted N-acylamidines of the general formula III which an be prepared in this way are filtered off with suction, washed and dried, or worked up extractively and fractionally distilled.

N'-Substituted N-acylamidines of the general formula III are suitable for preparing the catalysts of the general formula I according to the invention. To this end, a from about 0.05 to about 0.5 molar solution of an amidine of the general formula III and of a soluble transition metal compound, preferably compounds of palladium or platinum, for example palladium(II) acetylacetonate, bis(acetonitrile)palladium(II) chloride, dibenzylidenepalladium ($Pd_2(dba)_3$), bis(benzonitrile)palladium(II) chloride, platinum(II) acetylacetonate or bis(benzonitrile)platinum(II) chloride is advantageously prepared in a moderately polar, aprotic organic solvent. For this purpose, preference is given to using halogenated solvents, for example dichloromethane, chloroform, 1,2-dichloroethane, or aromatic solvents, for example benzene, toluene or xylene, or mixtures of the solvents mentioned. The solutions obtained in this way are covered with a layer of a suitable amount of a less polar solvent differing from the solvent or solvent mixture initially selected. Preference is given to halogen-free organic solvents having from 4 to 12 carbon atoms, particular preference to ethereal solvents having from 4 to 12 carbon atoms, for example diethyl ether or dibutyl ether.

In a preferred embodiment of the process according to the invention, N'-substituted N-acylamidine-palladium(II) complexes of the general formula I are obtained by dissolving 0.1 mmol of an N-acylamidine of the general formula III with 0.05 mmol (based on the number of palladium equivalents) of a soluble Pd(II) compound, preferably bis(benzonitrile)palladium(II) chloride, in from about 0.5 to about 3 ml of a polar halogenated solvent, preferably in dichloromethane or chloroform, and covering with from about 2 to about 20 ml of an etherial solvent, preferably diethyl ether.

On storage at temperatures between 0 and 40° C., the transition metal complexes according to the invention crystallize out of the solution. The crystallization time may vary widely and is typically between 1 h and 5 days. The crystals which are generally stable to air are filtered off with suction and dried.

N'-Substituted N-acylimidines of the general formula III are also suitable for preparing solutions of the catalysts of the general formula I. To this end, an about 0.0008 to 0.5 molar solution of the amidine of the general formula III and a soluble transition metal compound, preferably compounds of palladium or platinum, for example palladium(II) acetylacetonate, bis(acetonitrile)palladium(II) chloride, dibenzylidenepalladium ($Pd_2(dba)_3$), bis(benzonitrile)palladium(II) chloride, platinum(II) acetylacetonate or bis(benzonitrile)platinum(II) chloride, in a moderately polar, aprotic organic solvent is prepared. To this end, preference is given to using halogenated solvents, for example dichloromethane, chloroform, 1,2-dichloroethane or aromatic solvents, for example benzene, toluene or xylene, or mixtures of the solvents mentioned.

The invention further relates to the use of the transition metal compounds of the general formula I according to the invention or solutions thereof as catalysts for organic reactions, in particular for transition metal-catalyzed coupling reactions, in which at least one new chemical bond is formed between two carbon atoms. In addition to these C—C bond-forming reactions, the catalysts according to the invention are also suitable as catalysts for organic reactions in which new bonds are formed between carbon atoms and heteroatoms.

In the coupling reactions catalyzed by the transition metal complexes according to the invention, bonds can be formed between carbon atoms of the same or different hybridization. The carbon atoms to be bonded may each independently be $sp$-, $sp^2$- or $sp^3$-hybridized. This encompasses all coupling reactions between carbon atoms which are part of an alkyl, alkenyl, alkynyl or aryl or hetaryl system.

In particular, the transition metal compounds according to the invention are suitable as catalysts for Heck reactions, Suzuki couplings, Stephens-Castro-Sonogashira reactions and Stille couplings and further coupling reactions which are described extensively in the relevant technical literature and in which transition metal complexes soluble in organic solvents, especially those of the transition metals Pd, Pt, Ni, Cu, are customarily used. They are notable for an outstandingly high catalytic activity and also high temperature stability. The latter enables their use at high reaction temperatures, which is advantageous especially in the conversion of relatively unreactive substrates.

As is customary in the case of coupling reactions, the coupling reactions catalyzed by the transition metal compounds according to the invention can be optimized by a multitude of reagents, additives and promoters. For instance, Heck olefinations and Suzuki reactions are accelerated typically by the use of an auxiliary base, for example tri-n-butylamine, sodium acetate, potassium carbonate or cesium carbonate. Further customary additives or promoters whose function can in some cases not yet be explained are, for example, tetraphenyl-phosphonium chloride ($Ph_4PCl$) or tetra-n-butylammonium chloride ($Bu_4NCl$).

The invention is illustrated by the examples which follow, without restricting it to the specific embodiments mentioned:

EXAMPLES

Example 1

Synthesis of N-alkylamidines

General Method A

A baked-out and argon-purged Schlenk flask was initially charged with 60 mmol of a primary amine and 40 ml of absolute tetrahydrofuran. The solution was cooled to 78° C., and 37.5 ml (60 mmol) of n-butyllithium (1.6 M solution in n-hexane) were added dropwise with stirring. The mixture was allowed to thaw and stirred at room temperature for 30 minutes.

At −78° C., 60 mmol of the particular nitrile were slowly added dropwise with vigorous stirring. On completion of addition, stirring was continued at −78° C. for 1 hour, then the mixture was allowed to thaw and hydrolyzed by adding 40 ml of methanol and 40 ml of water. The organic phase was removed and the aqueous phase extracted using chloroform. The combined extracts were dried, the solvent was distilled off and the residue was fractionated under reduced pressure.

General Method B 0.15 mol of aromatic nitrile and 20 g (0.15 mol) of anhydrous aluminum trichloride were initially charged. 0.15 mol of the primary amine were added dropwise with ice cooling. On completion of addition, the mixture was heated to 180° C. for one hour. The melt was poured slowly onto a solution at 0° C. of 5 ml of concentrated hydrochloric acid and 400 ml of water. After adding 5 g of activated carbon, the mixture was stirred with cooling in a water bath for a further 20 minutes. The solids were filtered off. The filtrate was poured into a vigorously stirred solution at 0° C. of 55 g of sodium hydroxide in 300 ml of water. The aqueous phase was extracted using dichlorohexane. The combined organic phases were dried, the solvent was distilled off and the residue was fractionated under reduced pressure.

Example 2

Acylation of N-alkylamidines

General Method A 20 mmol of N-alkylamidine were initially charged in 25 ml of 2 M sodium hydroxide solution. At 0° C., a solution of 19 mmol of acyl chloride and 10 ml acetone was added dropwise with vigorous stirring. Subsequently, the mixture was stirred at a temperature of less than 10° C. for a further 1.5 hours. The precipitated product was filtered off with suction, washed with water and dried in an oil pump vacuum.

General Method B 10 mmol of N-alkylamidine and 10 ml of 2 M sodium hydroxide solution were initially charged. At 0° C., a solution of 9.5 mmol of acyl chloride and 5 ml of acetone was added dropwise with vigorous stirring. Subsequently, the mixture was stirred at a temperature of less than 10° C. for a further 1.5 hours. The organic phase was removed, and the aqueous phase extracted using chloroform. The combined extracts were dried and the residue was fractionated under reduced pressure.

Example 3

Preparation of bis(N-pivaloyl-N'-n-butylbenzamidine)palladium(II) chloride 26 mg (0.1 mmol) of N-pivaloyl-N'-n-butylbenzamidine and 19 mg (0.05 mmol) of bis(benzonitrile)palladium(II) chloride were dissolved in 1.5 ml of dichloromethane. The solution was covered with 10 ml of diethyl ether. Within a few hours, yellow, cuboidal crystals were formed. The product was filtered off with suction, washed with diethyl ether and dried under air. 31 mg (0.044 mmol, 89% of theory) of bis(N-pivaloyl-N'-n-butylbenzamidine)palladium(II) chloride were obtained.

Melting point: 227° C. (decomposition)

Example 4

Preparation of bis(N-pivalolyl-N'-n-propylbenzamidine)palladium(II) chloride 25 mg (0.1 mmol) of N-pivaloyl-N'-n-propylbenzamidine and 19 mg (0.05 mmol) of bis(benzonitrile)palladium(II) chloride were dissolved in 1 ml of chloroform. After 30 minutes, the mixture was covered with 12 ml of diethyl ether. The solution was stored at 35° C. Yellow, rhombic crystals were formed. After three days, the crystallization was complete. The product was filtered off with suction, washed with diethyl ether and dried under air.

27 mg (0.04 mmol, 81% of theory) of bis(N-pivalolyl-N'-n-propylbenzamidine)palladium(II) chloride were obtained.

Melting point 237° C. (decomposition)

Example 5

Preparation of bis(N-4-methylbenzoyl)-N'-n-propylbenzamidine)palladium(II) chloride 28 mg (0.1-mmol) of N-(4-methylbenzoyl)-N'-n-propylbenzamidine and 19 mg (0.05 mmol) of bis(benzonitrile)palladium(II) chloride were dissolved in 0.5 ml of chloroform. After 30 minutes, 2 ml of diethyl ether were added with stirring. The solution was covered with 10 ml of diethyl ether. Within from 3 to 5 days, the product crystallized out. The crystallization was terminated after two weeks. The product was filtered off with suction, washed with diethyl ether and dried under air.

27 mg (0.040 mmol, 81% of theory) of bis(N-(4-methylbenzoyl)-N'-n-propylbenzamidine)-palladium(II) chloride were obtained in the form of yellow, rodlike crystals.

Melting point 204° C. (decomposition)

Example 6

Catalysis of the Heck Reaction

The Heck couplings were carried out under standard reaction conditions where are described in the literature. To carry out the coupling reaction, a solution of aryl bromide and from 1.0 to 1.4 equivalents of olefin in the high-boiling solvent dimethylacetamide was admixed with 1.2 equivalents of auxiliary base and 2 mol % of catalyst. The reaction mixture was heated to from 100 to 140° C. Samples were taken regularly for gas chromatography (GC), in order to follow the progress of the reaction. After from one to seven days, the reaction was terminated. The production yield was determined by GC using an internal standard (diethylene glycol di-n-butyl ether). The simple specimen substrates used were bromobenzene and styrene, and the reaction product is unsubstituted trans-stilbene.

Phase transfer catalysts can act as promoters in palladium-catalyzed coupling reactions. The influence of tetra-n-butylammonium bromide ($Bu_4N^+Cl^-$) and tetraphenylphosphonium chloride ($Ph_4P^+Cl^-$) on the yield of the coupling reaction was investigated in several experiments.

The Heck coupling was carried out at various catalyst concentrations, reaction temperatures and in some cases with the addition of promoters. The substrates used were bromobenzene and styrene, which were converted to stilbene. The auxiliary bases used were tri-n-butylamine ($Bu_3N$) and sodium acetate (NaOAc). An overview of several catalysis mixtures is given by table 1.

TABLE 1

| | Heck reaction using bis(N-pivalolyl-N'-butylbenzamidine)palladium(II) chloride catalyst | | | |
|---|---|---|---|---|
| No. | Equivalents of olefin | Auxiliary base | Reaction conditions | Yield [%] |
| 1 | 1.4 | $Bu_3N$ | 140° C., 6 d | 9 |
| 2 | 1.0 | $Bu_3N$ | 100° C., 7 d | 12 |
| 3 | 1.4 | NaOAc | 100° C., 5 d | <1 |
| 4 | 1.4 | NaOAc | 140° C., 2 d | 87 |
| 5 | 1.4 | NaOAc | 140° C., 2 d 1 mol % of $Ph_4PCl$ | 73 |
| 6 | 1.4 | NaOAc | 140° C., 2 d 20 mol % of $Bu_4NCl$ | 81 |

Example 7

Catalysis of the Suzuki Reaction

The coupling of bromobenzene and benzeneboronic acid (dihydroxyphenylborane) to biphenyl was investigated. The typical reaction conditions were based on studies of the Suzuki reaction which were taken from the current literature.

To carry out the Suzuki cross-coupling, a mixture of bromobenzene and 1.2 equivalents of benzeneboronic acid in toluene was admixed with 2 equivalents of bis(N-pivaloyl-N'-butyl-benzamidine)palladium(II) chloride auxiliary base and as the catalyst. The reactions were carried out at from 85 to 110° C. To monitor the progress of the reaction, samples were taken regularly for was chromatography (GC). After from 1 to 72 hours, the reactions were terminated. The product yields were determined by GC using the internal standard diethylene glycol di-n-butyl Table 2 summarizes the coupling experiments of bromobenzene and benzeneboronic acid to give biphenyl under bis(N-pivaloyl-N'-butylbenzamidine)palladium(II) chloride catalysis.

TABLE 2

Suzuki reaction of bromobenzene with benzeneboronic acid under bis(N-pivaloyl-N'-butylbenzamidine)palladium(II) chloride catalysis

| No. | Catalyst concentration | Auxiliary base | Reaction conditions* | Yield [%] | TON** |
|---|---|---|---|---|---|
| 1 | 0.4 mol % | $K_2CO_3$ | 85° C., 1 h | >99 | 250 |
| 2 | 0.5 mol % | $K_2CO_3$ | 50° C., 48 h | 86 | 172 |
| 3 | 0.1 mol % | $K_2CO_3$ | 85° C., 3 h | 87 | 870 |
| 4 | 0.1 mol % | $K_2CO_3$ | 85° C., 24 h | 92 | 920 |
| 5 | 0.1 mol % | $K_2CO_3$ | 85° C., 72 h | 41 | 4100 |
| 6 | 0.1 mol % | $Cs_2CO_3$ | 85° C., 48 h | 35 | 3500 |
| 7 | 0.1 mol % | $K_2CO_3$ | 110° C., 24 h | 94 | 9400 |
| 8 | 0.0017 mol % | $K_2CO_3$ | 110° C., 4 h | 97 | 58000 |
| 9 | $4.5 \cdot 10^{-4}$ mol % | $K_2CO_3$ | 110° C., 3 h | 98 | 218000 |

*Coupling of 1.0 equivalent of bromobenzene and 1.2 equivalents of benzeneboronic acid, use of 2.0 equivalents of auxiliary base;
**Turnover number (TON) = mol (product)/mol (catalyst)

We claim:

1. An N'-substituted N-acylamidine-transition metal complex of the general formula I

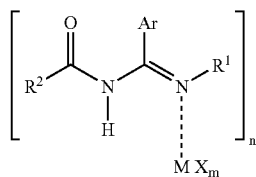

where
M is a transition metal selected from the group of the metals Ni, Cu, Ru, Rh, Pd, Os, Ir and Pt
X is Cl, Br, triflate, methanesulfonate or p-toluenesulfonate
m is 0, 1 or 2,
n is 1, 2 or 3
and the radicals are defined as follows:
$R^1$, $R^2$ are each a straight-chain, branched or cyclic hydrocarbon radical having from 1 to 20 carbon atoms which may be mono- or polyunsaturated, an aromatic radical having from 6 to 14 ring members which may be bonded directly or via a $C_1$- to $C_6$-alkyl or $C_2$- to $C_6$-alkylene group, and the radicals mentioned may bear one or more substituents selected from the group of $C_1$- to $C_6$-alkyl, $C_1$- to $C_4$-haloalkyl, $OR^3$, $NR^4R^5$, $COOR^6$, $Si(R^7)_3$, $Si(R^7)_2R^8$, halogen, aryl, $C_3$–$C_8$-cycloalkyl, $R^3$, $R^6$, $R^8$ are each independently $C_1$- to $C_{12}$-alkyl, $C_7$- to $C_{12}$-aralkyl, $C_6$- to $C_{10}$-aryl, $C_3$-to $C_8$-cycloalkyl, $C_3$- to $C_8$-cycloalkyl in which one $CH_2$ group has been replaced by O, NH or $NR^9$, $R^4$, $R^5$, $R^{10}$, $R^{11}$ are each independently hydrogen, straight-chain or branched $C_1$- to $C_{12}$-alkyl, $C_7$- to $C_{12}$-aralkyl, $C_6$- to $C_{10}$-aryl, $C_3$- to $C_8$-cycloalkyl or $C_3$- to $C_8$-cycloalkyl in which one $CH_2$ group has been replaced by O, NH or $N^9$, and $R^4$ and $R^5$ and/or $R^{10}$ and $R^{11}$ may each together be —$(CH_2)_y$—, where y is an integer from 4 to 7;

$R^7$, $R^9$ are each independently straight-chain or branched $C_1$- to $C_{12}$-alkyl or $C_7$- $C_{12}$-aralkyl, Ar is $C_6$–$C_{10}$-aryl or hetaryl having from 5 to 10 ring members, and the radicals mentioned may be substituted by $C_1$- to $C_6$-alkyl, $C_1$- to $C_4$-haloalkyl, $NR^{10}R^{11}$, $COOR^6$, $Si(R^7)_3$, $Si(R^7)_2R^8$, $OR^3$ and/or halogen.

2. A transition metal complex of the formula I as claimed in claim 1 where M is a transition metal selected from the group of Ru, Rh, Os, Ir, Pd and Pt.

3. A transition metal complex of the formula I as claimed in claim 1 where M is Pd or Pt and m and n are each 2.

4. A transition metal complex of the formula I as claimed in claim 1,
where
$R^1$ and $R^2$ are each branched or unbranched $C_1$- to $C_{12}$-alkyl, $C_7$- to $C_{12}$-aralkyl, $C_6$- to $C_{10}$-aryl, and the radicals mentioned may be substituted by from one to three halogen atoms and/or one or two $C_1$–$C_6$-alkyl, trifluoromethyl and/or $C_1$- to $C_6$-alkoxy substituents, and
Ar is $C_6$–$C_{10}$-aryl or hetaryl having 5 or 6 ring members, and the radicals mentioned may be substituted by one or more $C_1$- to $C_6$-alkyl, $C_1$- to $C_6$-alkoxycarbonyl, $C_1$- to $C_6$-alkoxy, trialkylsilyl or diarylalkylsilyl and/or trifluoromethyl substituents and/or halogen.

5. A process for preparing N'-substituted N-acylamidine-transition metal complexes of the general formula I as claimed in claim 1, which comprises dissolving an N'-substituted N-acylamidine ligand of the formula III

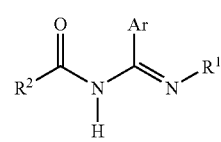

and a transition metal compound containing the central atom M according to formula I in an organic solvent or in a mixture of different organic solvents and crystallizing the N'-substituted N-acylamidine-transition metal complex by adding a further solvent different to the solvent or solvent mixture used initially.

6. A process as claimed in claim 5, wherein the first solvent used is a halogenated or aromatic solvent or a mixture of different halogenated or aromatic solvents, and an ethereal solvent or solvent mixture is added for crystallization.

7. A catalyst which comprises the N'-substituted N-acylamidine-transition metal complex of the formula I as claimed in claim 1.

8. The catalyst as claimed in claim 7 for transition metal-catalyzed coupling reactions in which at least one new bond is formed between two carbon atoms.

9. In an olefination process wherein the improvement comprises using the catalyst as claimed in claim 7.

10. In an alkynylation process wherein the improvement comprises using the catalyst as claimed in claim 7.

11. In an arylation process wherein the improvement comprises using the catalyst as claimed in claim 7.

12. In a diaryl coupling reaction process wherein the improvement comprises using the catalyst as claimed in claim 7.

13. In a Heck reaction wherein the improvement comprises using the catalyst as claimed in claim 7.

14. In a Suzuki coupling reaction wherein the improvement comprises using the catalyst as claimed in claim 7.

15. In a Stephens-Castro-Sonogashira reaction wherein the improvement comprises using the catalyst as claimed in claim 7.

16. In a Stile coupling reaction wherein the improvement comprises using the catalyst as claimed in claim 7.

17. A coupling reaction which comprises reacting a base in the presence of the catalyst as claimed in claim 7.

* * * * *

UNITED STATES PATENT AND TRADEMARK OFFICE
CERTIFICATE OF CORRECTION

PATENT NO. : 7,141,687 B2 Page 1 of 1
APPLICATION NO. : 10/537569
DATED : November 28, 2006
INVENTOR(S) : Jan Kurt Eberhardt et al.

It is certified that error appears in the above-identified patent and that said Letters Patent is hereby corrected as shown below:

In Claim 1, at column 12, line 15, "replaced by O, NH, or $N^9$, and $R^4$ and $R^5$ and/or $R^{10}$ and" should read -- replaced by O, NH, or $NR^9$, and $R^4$ and $R^5$ and/or $R^{10}$ and --.

Signed and Sealed this

Twenty-seventh Day of March, 2007

JON W. DUDAS
*Director of the United States Patent and Trademark Office*